United States Patent
Lee et al.

(10) Patent No.: US 12,161,999 B2
(45) Date of Patent: *Dec. 10, 2024

(54) COBALT-BASED SINGLE-ATOM DEHYDROGENATION CATALYSTS AND METHOD FOR PRODUCING CORRESPONDING OLEFINS FROM PARAFFINS USING THE SAME

(71) Applicants: SK Innovation Co., Ltd., Seoul (KR); SK Geo Centric Co., Ltd., Seoul (KR)

(72) Inventors: Ho Won Lee, Daejeon (KR); Je Mi Lim, Daejeon (KR); Hee Soo Kim, Daejeon (KR); Ju Hwan Im, Busan (KR); Dae Hyun Choo, Asan-si (KR); Ka Young Kim, Daejeon (KR); Jae Suk Choi, Daejeon (KR)

(73) Assignees: SK Innovation Co., Ltd., Seoul (KR); SK Geo Centric Co., Ltd., Seoul (KR)

(*) Notice: Subject to any disclaimer, the term of this patent is extended or adjusted under 35 U.S.C. 154(b) by 130 days.

This patent is subject to a terminal disclaimer.

(21) Appl. No.: 17/289,271

(22) PCT Filed: Oct. 30, 2019

(86) PCT No.: PCT/KR2019/014476
§ 371 (c)(1),
(2) Date: Apr. 28, 2021

(87) PCT Pub. No.: WO2020/091418
PCT Pub. Date: May 7, 2020

(65) Prior Publication Data
US 2021/0394160 A1    Dec. 23, 2021

(30) Foreign Application Priority Data
Oct. 31, 2018    (KR) .................. 10-2018-0132182

(51) Int. Cl.
*B01J 23/75* (2006.01)
*B01J 21/08* (2006.01)
(Continued)

(52) U.S. Cl.
CPC ............... *B01J 23/75* (2013.01); *B01J 21/08* (2013.01); *B01J 37/02* (2013.01); *B01J 37/0205* (2013.01);
(Continued)

(58) Field of Classification Search
CPC ........ B01J 21/08; B01J 23/75; B01J 37/0207; B01J 37/0209; B01J 37/0213
See application file for complete search history.

(56) References Cited

U.S. PATENT DOCUMENTS

| 4,639,430 A | 1/1987 | Pasquet et al. |
| 5,347,046 A | 9/1994 | White et al. |

(Continued)

FOREIGN PATENT DOCUMENTS

| CN | 86103269 A | 12/1986 |
| CN | 1123527 A | 5/1996 |

(Continued)

OTHER PUBLICATIONS

Machine translation of CN111252772, publication date Jun. 9, 2020.*

(Continued)

*Primary Examiner* — Jun Li
(74) *Attorney, Agent, or Firm* — The Webb Law Firm (57) ABSTRACT

In the present disclosure, a dehydrogenation catalyst in which cobalt in the form of single atom is supported on an inorganic oxide (specifically, silica) support in which an alkali metal in the form of single atom is fixed by alkali metal pretreatment and a method for producing the same, and a method for producing olefins by dehydrogenating (Continued)

corresponding paraffins, specifically light paraffins in the presence of the dehydrogenation catalyst are described.

11 Claims, 4 Drawing Sheets

(51) Int. Cl.
    *B01J 37/00*      (2006.01)
    *B01J 37/02*      (2006.01)
    *B01J 37/08*      (2006.01)
    *C07C 5/333*      (2006.01)

(52) U.S. Cl.
    CPC ....... *B01J 37/0207* (2013.01); *B01J 37/0209* (2013.01); *B01J 37/0213* (2013.01); *B01J 37/08* (2013.01); *C07C 5/3335* (2013.01); *C07C 2521/08* (2013.01); *C07C 2523/75* (2013.01)

(56) References Cited

U.S. PATENT DOCUMENTS

| | | | |
|---|---|---|---|
| 5,453,558 A | 9/1995 | Alexander et al. | |
| 5,475,144 A | 12/1995 | Watson et al. | |
| 6,103,103 A | 8/2000 | Alexander et al. | |
| 6,197,717 B1* | 3/2001 | Alexander | B01J 29/86 502/66 |
| 6,733,657 B2 | 5/2004 | Benazzi et al. | |
| 8,680,357 B1* | 3/2014 | Rokicki | B01J 23/002 585/663 |
| 9,504,991 B2* | 11/2016 | York | G06F 11/3632 |
| 10,040,054 B2 | 8/2018 | Rytter et al. | |
| 11,420,191 B2* | 8/2022 | Lee | B01J 23/75 |
| 2010/0166648 A1* | 7/2010 | Lefenfeld | B01J 23/04 423/657 |
| 2010/0185010 A1 | 7/2010 | Hagemeyer et al. | |
| 2012/0016171 A1 | 1/2012 | Kustov et al. | |
| 2013/0253248 A1 | 9/2013 | Gamoras et al. | |
| 2014/0128563 A1 | 5/2014 | McDaniel et al. | |
| 2014/0274672 A1 | 9/2014 | Kauffman et al. | |
| 2014/0275686 A1 | 9/2014 | Hock et al. | |
| 2015/0141593 A1 | 5/2015 | Yang et al. | |
| 2016/0074838 A1 | 3/2016 | Hock et al. | |
| 2016/0199814 A1 | 7/2016 | Bai et al. | |
| 2018/0229220 A1 | 8/2018 | Dang et al. | |
| 2019/0232255 A1* | 8/2019 | Jo | B01J 23/626 |
| 2021/0170370 A1* | 6/2021 | Lee | B01J 23/78 |
| 2021/0402379 A1* | 12/2021 | Cheon | B01J 37/08 |

FOREIGN PATENT DOCUMENTS

| | | | |
|---|---|---|---|
| CN | 1151722 A | 6/1997 | |
| CN | 1151723 A | 6/1997 | |
| CN | 101108362 A | 1/2008 | |
| CN | 104525183 A | 4/2015 | |
| CN | 111252772 A | 6/2020 | |
| EP | 3928864 A1 | 12/2021 | |
| JP | 200829949 A | 2/2008 | |
| JP | 2013505996 A | 2/2013 | |
| JP | 2013511383 A | 4/2013 | |
| KR | 100837195 B1 | 6/2008 | |
| KR | 1020090116054 A | 11/2009 | |
| KR | 1020180041794 A | 4/2018 | |
| KR | 1020200049209 A | 5/2020 | |
| KR | 20210018566 A | 2/2021 | |
| WO | 9633015 A1 | 10/1996 | |
| WO | WO-2009136711 A2 * | 11/2009 | ............. B01J 23/75 |

OTHER PUBLICATIONS

Schweitzer et al., "Propylene Hydrogenation and Propane Dehydrogenation by a Single-Site Zn2+ on Silica Catalyst", ACS Catalysis, 2014, pp. 1091-1098, vol. 4.

Keyvanloo et al., "Supported Iron Fischer-Tropsch Catalyst: Superior Activity and Stability Using a Thermally Stable Silica-Doped Alumina Support", American Chemical Society Catalysis, 2014, pp. 1071-1077, vol. 4.

Silica—Silicon Dioxide (SiO2). Properties [online]. AZO Materials, 2001 [retrieved on Dec. 10, 2021]. Retrieved from the Internet: <URL: https://www.azom.com/properties.aspx?ArticleID=1114>.

Zhao et al., "Zirconium Modification Promotes Catalytic Activity of a Single-Site Cobalt Heterogeneous Catalyst for Propane Dehydrogenation" American Chemical Society Omega, 2018, pp. 11117-11127, vol. 3.

Zirconia—ZrO2, Zirconium Dioxide. Properties [online]. AZO Materials, 2001 [retrieved on Dec. 10, 2021]. Retrieved from the Internet: <URL: https://www.azom.com/properties.aspx?ArticleID=133>.

Goldsmith et al., "Beyond Ordered Materials: Understanding Catalytic Sites on Amorphous Solids", ACS Catal., 2017, pp. 7543-7557, vol. 7.

Jimenez et al., "Influence of coordination environment of anchored single-site cobalt catalyst on CO2 hydrogenation", ChemCatChem, 2019, pp. 1-10.

\* cited by examiner

COBALT-BASED SINGLE-ATOM DEHYDROGENATION CATALYSTS AND METHOD FOR PRODUCING CORRESPONDING OLEFINS FROM PARAFFINS USING THE SAME

CROSS-REFERENCE TO RELATED APPLICATIONS

This application is the United States national phase of International Application No. PCT/KR2019/014476 filed Oct. 30, 2019, and claims priority to Korean Patent Application No. 10-2018-0132182 filed Oct. 31, 2018, the disclosures of which are hereby incorporated by reference in their entirety.

BACKGROUND OF THE INVENTION

Field of the Invention

The present disclosure relates to cobalt-based single-atom dehydrogenation catalysts and a method for producing olefins from corresponding paraffins using the same. More specifically, the present disclosure relates to a dehydrogenation catalyst in which cobalt in the form of single atom is supported on an inorganic oxide (specifically, silica) support in which an alkali metal in the form of single atom is fixed by alkali metal pretreatment and a method for producing the same, and a method for producing olefins by dehydrogenating corresponding paraffins, specifically light paraffins in the presence of the dehydrogenation catalyst.

DESCRIPTION OF RELATED ART

Light olefins such as ethylene, propylene, and butylene are widely used in the petrochemical industry and are an important chemical raw material used as a building block for chemical products (oxo-alcohol, acrylonitrile, propylene oxide, butanol, acrylic acid and the like) and plastic products (polypropylene, ethylene-propylene rubber and the like). In particular, propylene is a colorless, low boiling point compound and is usually traded typically at a polymer grade (at least about 99.5% purity), chemical grade (about 90 to 96% purity), and refinery grade (about 50% to 70% purity).

In general, these light olefins are produced by thermal cracking of naphtha or kerosene under supply of steam (namely, steam cracking). However, as the demand for light olefins has recently increased, it is difficult to meet the increasing demand by the thermal cracking method. In response to the demand, various synthetic methods (for example, catalytic cracking of light fractions, etc.) have been proposed. The products obtained by the steam cracking, catalytic cracking process, and the like are typically a mixture of various hydrocarbons including methane, ethane, propane, and C5/C6+ paraffinic hydrocarbons as well as olefins (ethylene, propylene, etc.).

At this time, the composition of the product mixture may be adjusted by modifying the operation conditions of the processes. However, this is not a sufficient option when the market demand for a particular product is higher than those for other co-products. For example, the market demand for propylene is rapidly increasing as compared to that for ethylene in many regions. Such low olefin yields which conventional commercial processes suffer require catalyst reaction technologies for increasing selectivity for olefins as much as possible.

As a recently commercialized process, a manufacturing process by a dehydrogenation reaction is known. Illustratively, paraffins may be converted into the corresponding olefins through the dehydrogenation reaction according to Reaction Scheme 1 below.

$$C_3H_8 \leftrightarrow C_3H_6 + H_2; C_4H_{10} \leftrightarrow i\text{-}C_4H_8 + H_2 \qquad \text{[Reaction Scheme 1]}$$

The above-described dehydrogenation reaction eliminates hydrogen molecules from paraffins to form olefinic double bonds. Such a dehydrogenation reaction of light paraffins selectively produces the corresponding olefins (specifically propylene) from light paraffins (specifically propane) as a feedstock, and the reaction typically takes place for a short residence time through an endothermic reaction at high temperatures. Such dehydrogenation of paraffins corresponds to a complex chemical process, and this is because thermodynamic equilibrium limits the possible conversion per pass and a large amount of heat is required to be supplied for the reaction.

Examples of currently commercialized dehydrogenation technologies are presented in Table 1 below.

TABLE 1

|  | CATOFIN | Oleflex | Uhde | SABIC |
|---|---|---|---|---|
| Developer Reactor | Lummus Insulation fixed bed | UOP Insulation moving bed | Lrupp-Uhde DH + ODH- insulation | SABIC Insulation fixed bed and FBR |
| Operation mode | Cyclic | Continuous | Cyclic | Cyclic |
| Feedstock | C3-C4 | C3-C4 | C3-C4 | C3 |
| Catalyst | Chromium-based supported catalyst | Pt-Sn-based supported catalyst | Pt-Sn-based supported catalyst | Pt-Sn-based supported catalyst |
| Reaction temperature (° C.) | 565 to 649 | 550 to 620 | DH: 550 to 590 ODH: about 600 | 560 to 600 |
| Reaction pressure (bar) | 03 to 0.5 | 2 to 3 | 5 to 6 | 0.1 to 6 |
| Cycle time | 15 to 30 minutes | — | 8 hours | 15 to 30 minutes |

For the commercial processes exemplified above, a feedstock in a mixed gas form is supplied while chromium- or platinum-based (e.g., Pt—Sn) catalysts are mainly employed. Iron oxide-based catalysts and gallium/zeolite catalysts are also known to be applicable to the dehydrogenation of paraffins. In addition, although generally undergoing a regeneration process after being inactivated with the generation of coke during reactions, dehydrogenation catalysts are required to maintain catalytic activity during multiple cycles of regeneration.

In recent years, there has been a growing interest in catalyst technology for utilizing all metal elements supported on a support. Conventional metal-supported catalysts have catalytic metal particles assembled on the supports. Given a broad size distribution and irregular morphologies, the assembled metal particles cannot take full advantage of metal active sites and thus have undesirable influence on catalyst activity or selectivity. In contrast, single-atom catalysts provide the advantage that catalyst activity can be maximized by downsizing metal nanostructures to metal active sites distributed to an atomic level. In this regard, there is a technique known to convert propane to propylene through dehydrogenation in the presence of a catalyst having a single-atom type active metal (e.g., zinc) supported onto a support such as silica (e.g., ACS Catal. 2014, 4, 4, 1091-1098). In this document, a mixed gas containing 3% of propane and the balance of argon (Ar), which is an inert gas, is used as a reactant with the aim of selectively converting paraffins to the corresponding olefins while suppressing the formation of by-products. However, a feedstock containing a low content of paraffins is improper from the viewpoint of commerce. Furthermore, the catalyst may be thermally unstable in a high temperature reaction of about 500 to 600° C. and in a dehydrogenation processes that proceed in high temperature and regeneration conditions because the catalyst is thermally treated at as low as of 300° C.

Catalysts in which cobalt other than the previously known active metals is supported on various inorganic oxide supports are also known to have activity in the dehydrogenation reaction of paraffins (for example, US Patent Publication No. 2013-0253248). At this time, it may be considered to conduct the dehydrogenation in the presence of a catalyst in which cobalt as an active metal is supported on a support in the form of single atom, but in this case, the agglomeration phenomenon of the cobalt elements fixed on the support or the phenomenon in which cobalt metal is partially formed by reduction occurs in the course of the dehydrogenation conducted at a high temperature, and thus there is a limit to securing of long-term reaction stability.

Hence, there has not been known any method for suppressing a phenomenon in which the active metal in the form of single atom loaded on the support is reduced or agglomerated in the course of the dehydrogenation of light paraffins and the catalytic activity is deteriorated while maximizing the advantages of the single atom cobalt-supported catalyst.

In the prior researches, a feedstock containing paraffins at a low content is used for the dehydrogenation. Accordingly, there is a need for a method capable of stably producing olefins with a high conversion and selectivity even when high concentration (high content) of paraffins, further pure paraffins are used as a feedstock for commercialization.

SUMMARY OF INVENTION

Technical Problem

An embodiment according to the present disclosure provides a cobalt-based single-atom catalyst for dehydrogenation capable of maintaining catalytic stability or long-term activity even when being exposed to a high temperature in the course of the production of olefins through the dehydrogenation of paraffins and a method for producing the same.

An embodiment according to the present disclosure also provides a dehydrogenation process having an desirable conversion of paraffin even for a feedstock containing paraffins at a high concentration and excellent selectivity for corresponding olefins so as to be suitable for commercialization.

Solution to Problem

According to a first aspect of the present disclosure, there is provided a method for preparing a cobalt-based single-atom catalyst, the method comprising:
a) preparing a silica-containing aqueous dispersion;
b) dissolving a salt of an alkali metal in the silica-containing aqueous dispersion to give an aqueous dispersion of alkali metal-treated silica;
c) adjusting a pH of the aqueous dispersion of alkali metal-treated silica to at least 10 by adding a base to the aqueous dispersion to give a pH-adjusted aqueous dispersion of alkali metal-treated silica, wherein at least a part of alkali metal ions are electrostatically adsorbed on the surface of the silica;
d) separately preparing an aqueous solution of a cobalt precursor having an oxidation number of 3+ and adjusting a pH of the aqueous solution of a cobalt precursor to at least 10 adding a base to the aqueous solution to give a pH-adjusted aqueous cobalt precursor solution;
e) combining the pH-adjusted aqueous dispersion of alkali metal-treated silica with the pH-adjusted aqueous cobalt precursor solution to give an aqueous dispersion in which at least a part of cobalt ions having an oxidation number of 3+ are electrostatically adsorbed on the surface of the alkali metal ion-adsorbed silica;
f) removing an alkali metal and cobalt that are not adsorbed on the surface of the silica from the aqueous dispersion of the cobalt ion, alkali metal ion-adsorbed silica; and
g) heat treating the cobalt ion, alkali metal ion-adsorbed silica resulting from the step f),
wherein the cobalt having an oxidation number of 2+ and the alkali metal having an oxidation number of 1+, respectively, exist in an isolated form of single atom on the silica while the cobalt having an oxidation number of 2+ forms a tetrahedrally coordinated at the three-membered siloxane ring present on the surface of silica.

According to a second aspect of the present disclosure, there is provided a dehydrogenation catalyst that is a cobalt-based single-atom catalyst comprising:
silica having an alkali metal adsorbed thereon as a support; and
cobalt, as an active metal, loaded on the support, wherein the cobalt having an oxidation number of 2+ and the alkali metal having an oxidation number of 1+, respectively, exist in an isolated form of single atom on the silica while the cobalt having an oxidation number of 2+ forms a tetrahedrally coordinated at the three-membered siloxane ring present on the surface of silica.

According to a third aspect of the present disclosure, there is provided a method for producing an olefin from a paraffin, the method comprising:
providing a feedstock containing a light paraffin;
subjecting the feedstock to dehydrogenation at a temperature of 500° C. to 700° C. under a pressure of 0.3 to 2 bar in presence of the catalyst described above; and
recovering the olefin corresponding to the light paraffin from the dehydrogenation product.

Advantageous Effects of Invention

According to an embodiment according to the present disclosure, the dehydrogenation catalyst has single-atom cobalt loaded on an alkali metal-adsorbed silica support. This catalyst can effectively suppress the agglomeration of cobalt atoms or sintering by virtue of the action of the alkali metal attached to the surface of the silica surface in the form of single atom even when exposed to a high temperature (for example, about 500° C. or more) in the course of the conversion of paraffins, particularly light paraffins into the corresponding olefins through the dehydrogenation. Because of such improved thermal stability, the dehydrogenation catalyst has an advantage of maintaining the catalytic activity for a long time since the degradation or denaturation of the catalyst is effectively suppressed even when the catalyst is exposed to a high temperature for a long time during the dehydrogenation or comes into contact with hydrogen generated from the dehydrogenation.

The catalyst according to embodiments of the present disclosure has an advantage particularly desirable in the aspect of commercialization since the catalyst can have a favorable conversion and olefin selectivity even for a feedstock containing paraffins at a high content in the dehydrogenation.

DESCRIPTION OF THE INVENTION

The present invention can all be achieved by the following description. The following description should be understood as describing a preferred embodiment of the present invention, and the present invention is not necessarily limited thereto. In addition, it should be understood that the accompanying drawings are provided to aid understanding and the present invention is not limited thereto.

The terms used herein may be defined as follows.

The term "heterogeneous catalyst" refers to a catalyst that is present in a different phase from a reactant in a catalyst reaction process. For example, a heterogeneous catalyst may remain undissolved in a reaction medium. When a heterogeneous catalyst is given, the onset of a reaction occurs with the diffusion and adsorption of reactants onto the surface of the heterogeneous catalyst. After completion of the reaction, a product needs to be desorbed from the surface of the heterogeneous catalyst.

The term "support", as used herein, refers to a material (typically a solid-phase material) with a high specific surface area, to which a catalytically active component is attached, and the support may or may not be involved in a catalytic reaction.

The term "crystalline" refers typically to any solid substance in which atoms are arranged to have a lattice structure (e.g., a three-dimensional order) while the term "amorphous" refers to any solid substance that does not have such a lattice structure. The substances may each be identified by X-ray diffraction (XRD), nuclear magnetic resonance (NMR), differential scanning calorimetry (DSC), or a combination thereof.

The term "light paraffin" refers to a paraffin of 2 to 5 carbon atoms, more particularly, a paraffin of 3 or 4 carbon atoms, as exemplified by ethane, propane, n-butane, isobutane and pentane. In addition, "corresponding olefin" refers to an olefin resulting from the removal of a hydrogen molecule from a light paraffin in a feedstock by dehydrogenation and thus having the same number of carbon atoms as the paraffin.

The term "silica", as used herein, refers to a substance of tetrahedral coordination in which four oxygen atoms bind to one silicon atom.

As used herein, the term "porous silica" refers to a three-dimensional network silica having porosity, which may be composed of an aggregate of primary silica particles.

Dehydrogenation Catalyst

According to an embodiment of the present disclosure, there is provided a cobalt-based single-atom catalyst which not only is suitable for conversion of a feedstock containing paraffins (specifically, light paraffins) at a high concentration into the corresponding olefins with a desirable conversion and selectivity, but also exhibits favorable thermal stability even when being exposed to a high temperature during the dehydrogenation.

According to an embodiment, the catalyst may be a heterogeneous catalyst in which cobalt in the form of single atom as an active metal is loaded (supported) on a silica-based support (specifically, an amorphous silica support) in which an alkali metal is fixed (adsorbed) in the form of single atom (namely, treated with an alkali metal).

In the case of the alkali metal-adsorbed silica support, a positively charged alkali metal (or alkali metal ion) having an oxidation number of 1+ is bound to silica in the form of an isolated single atom by electrostatic interaction (or adsorption) with negatively charged SiO$^-$ on the surface of silica. Cobalt (Co(II)) or cobalt ions having an oxidation number of 2+ exist in the form of an isolated single atom on the surface of silica, and the cobalt in a single-atom form is tetrahedrally coordinated at the three-membered siloxane ring present on the surface of silica.

As such, the alkali metal in the form of single atom is introduced to silica support, before cobalt is supported (or loaded) on the silica, to define the sites available for supporting cobalt, and as a result, the alkali metal is interposed between cobalt atoms, thus effectively suppressing the aggregation or agglomeration caused by polygomerization, such as dimerization between cobalt atoms.

In addition, with the introduction of an alkali metal thereto, the catalyst according to the present embodiment exhibits an increased resistance against the reduction of the cobalt in an oxidation state to an elemental state by hydrogen generated upon the dehydrogenation and thus advantageously resists a sharp decrease in activity during the reaction.

The function resulting from the introduction of the alkali metal to the catalyst is conceptually distinguished from the use of an alkali metal as a promoter in the conventional catalysts which provides the functions of controlling strong acid sites present in the supports rather than central metal ingredients to suppress strong acid site-induced dissociation of carbon-carbon bonds in paraffins or coke formation, thereby increasing the selectivity of the catalytic reaction and preventing the catalyst deactivation caused by coke.

In the present embodiment, the introduction of an alkali metal aims to control the loading site and/or amount of cobalt as the central metal, which is locally concentrated and is thus liable to aggregate, unlike the function as a promoter as in the conventional dehydrogenation catalysts. Theoretically, thus, the alkali metal may interfere with the catalytic reactions. In the embodiment, however, the introduction of an alkali metal is considered to provide the advantage of increasing the stability of the catalyst by ultimately suppressing the reduction and/or aggregation of the cobalt metal while minimizing those disadvantages. Specifically, the cobalt supported in the form of single atom without treatment with an alkali metal undergoes Co—O—Co dimer formation and aggregation during the dehydrogenation. When such catalyst is exposed to high temperatures with the progression of the reaction or when dehydrogenation is conducted using a feedstock containing a high concentration of paraffins, the afore-mentioned problems notably arise, thus decreasing the catalytic activity.

According to an exemplary embodiment, the alkali metal may be at least one selected from the group consisting of sodium (Na), potassium (K), and cesium (Cs). More specifically, potassium (K) may be used as an alkali metal because potassium has an ion size which enables it to be located around cobalt bound to the 3-membered siloxane ring such that effective stabilization might be realized in cooperation with cobalt.

In this regard, the content of the alkali metal in the dehydrogenation catalyst may be in a range of, for example, about 0.00001% to 1% by weight, specifically about 0.0001% to 0.5% by weight, more specifically about 0.004% to 0.1% by weight.

According to an exemplary embodiment, the dehydrogenation catalyst contains cobalt at a content (loading amount) of, for example, about 0.1% to 10% by weight, specifically about 0.5% to 5% by weight, more specifically about 1% to 3% by weight. The loading amount may slightly vary depending on properties of the silica support, but may be controlled taking into account the maximum amount of the cobalt existing in a single atom, typically in a range of about 2 to 3% by weight. At this time, the weight ratio of cobalt (Co)/alkali metal in the catalyst may range, for example, from about 1 to about 2000, specifically from about 10 to about 1000, more specifically from about 100 to about 500.

An excessive loading amount of cobalt relative to the alkali metal accounts for the presence of redundant cobalt ions within a locally restricted area. In this circumstance, deficiency of the alkali metal component could cause the reduction or aggregation of cobalt ions on the surface of catalyst, resulting in the deactivation of the cobalt single-atom catalyst. On the other hand, when the relative loading amount of cobalt to the alkali metal is too small, the alkali metal occupies relatively much space to act as a barrier against the access of the reactant light paraffin to the catalyst, greatly reducing the conversion. In consideration of this, the weight ratio of cobalt (Co)/alkali metal may be advantageously adjusted within the range as describe above.

Method for producing dehydrogenation catalyst According to an embodiment, a method for producing a cobalt-based single-atom dehydrogenation catalyst is as follows. First, silica is added to an aqueous medium to prepare an aqueous dispersion containing silica (step a). At this time, the silica is not limited to a specific one, but it may be advantageous to use high-purity silica having as little impurity content as possible.

According to a specific embodiment, silica may be an amorphous silica, specifically a porous amorphous silica, and for example, fumed silica, wet (precipitated) silica, and the like. Given as a fine powder, such silica has a large amount of silanol groups and siloxane groups present on the molecule surface thereof. The silanol (hydroxyl) groups on the silica surface may exist in the three types: isolated (Si—OH), vicinal (linked through a hydrogen bond), and germinal (HO—Si—OH).

According to an exemplary embodiment, the specific surface area (BET specific surface area) of silica may be in a range of, for example, at least about 100 $m^2/g$, specifically about 200 to 1500 $m^2/g$, more specifically about 300 to 1000 $m^2/g$. The pore volume of silica may be in a range of, for example, about 0.1 to 10 $cm^3/g$, specifically about 0.3 to 5 $cm^3/g$, more specifically about 0.5 to 3 $cm^3/g$. Further, the pore size (average diameter) may be in a range of, for example, about 0.5 to 200 nm, specifically about 1 to 100 nm, more specifically about 3 to 30 nm. It should be understood that the above numerical ranges have been described for illustrative purposes.

The aqueous medium used to prepare the silica-containing aqueous dispersion may be water, specifically distilled water. The amount of silica in the aqueous dispersion may be in a range of, for example, about 1% to 30% by weight, specifically about 3% to 20% by weight, more specifically about 5% to 10% by weight.

Thereafter, a salt of alkali metal is added to and dissolved in the silica-containing aqueous dispersion to prepare an aqueous dispersion of alkali metal-treated silica (step b).

Illustratively, the salt of an alkali metal is not particularly limited but may be, for example, at least one selected from a hydroxide, a nitrate, a chloride, a carbonate, and a sulfate of the alkali metal. More specifically, a hydroxide of the alkali metal may be used, because this type of salt is advantageous in pH control without causing the coprecipitation of a cobalt precursor.

According to an exemplary embodiment, the salt of alkali metal may be added and dissolved in an appropriate amount, for example in a range of about 0.001% to 3% by weight, specifically about 0.005% to 1% by weight, more specifically about 0.01% to 0.5% by weight based on the weight of silica in the aqueous dispersion.

Next, a base is added to the alkali metal-treated silica-containing aqueous dispersion to prepare a pH-adjusted aqueous dispersion of alkali metal-treated silica (step c).

By the addition of the base, the pH of the alkali metal-treated silica-containing aqueous dispersion may be adjusted to a range of, for example, at least about 10, specifically at least about 11, more specifically about 10.5 to 11.5. The reason for increasing the pH of the alkali metal-treated silica-containing aqueous dispersion is to deprotonate the silica surface. Specifically, hydrogen ions ($H^+$) may be eliminated from the silanol group (Si—OH) present on the silica surface to impart a negative charge. In other words, since ions are not adsorbed at the point of zero charge (PZC) of silica and silanol groups (hydroxy groups) are maintained, the silica surface is negatively charged by deprotonation through pH adjustment.

As a result, the alkali metal ions may be fixed (or immobilized) or grafted in the form of single atom onto the silica by the electrostatic interaction (that is, by electrostatic adsorption) with the silanol anion ($SiO^-$) on the deprotonated silica surface. In addition, the siloxane (specifically, the 3-membered siloxane) that coexists with silanol on the silica surface forms three silanol anions in the basic aqueous medium, which are considered to provide sites to which cobalt can be fixed or immobilized in a form of single atom in a subsequent step.

According to an exemplary embodiment, the base may be, for example, an aqueous solution of sodium hydroxide, potassium hydroxide, ammonium hydroxide or the like, specifically, an ammonium-containing base, more specifically, ammonium hydroxide (ammonia water) may be used. Advantageously, the base added should not cause precipitation in the subsequent step in which an aqueous solution of a cobalt precursor is combined or mixed therewith.

According to an embodiment of the present disclosure, apart from the step of preparing a pH-adjusted aqueous dispersion of alkali metal-treated silica, a step of preparing an aqueous solution of a cobalt precursor and adding a base to the aqueous solution to prepare a pH-adjusted aqueous solution of cobalt precursor may be performed (step d).

In this regard, the cobalt precursor may include a cobalt (Co(III)) complex ion having an oxidation number of 3+. For example, $Co(NH_3)_6Cl_3$ may be directly used or at least one cobalt compound (precursor) selected from $Co(NO_3)_2$, $CoCl_2$, and $Co(acac)_3$ is treated with ammonia water and filtered to obtain a precursor including a cobalt complex ion. The employment of $Co(NH_3)_6Cl_3$ may be advantageous for easygoing formation of a cobalt single-atom catalyst because it can minimize the preparations steps.

In an exemplary embodiment, the aqueous solution of precursor may contain a cobalt precursor at a concentration of, for example, about 0.1% to 20% by weight, specifically about 0.5% to 10% by weight, more specifically about 1% to 5% by weight.

Further, the pH of the cobalt precursor solution may be adjusted by addition of a base (an alkaline ingredient). The pH adjustment enables the surface of the silica to stably retain a deprotonated state (that is, modified to have a negative charge) in the subsequent step of combining or contacting with the alkali metal-treated, silica support, whereby the positively charged cobalt ions ($Co^{3+}$) of the precursor can be fixed or attached to the silica surface through electrostatic adsorption.

As such, the base added to the cobalt precursor solution may be at least one selected from those used in step c. Illustratively, the same base or base compound may be used in both step c and step d. Even in this case, the base that does not cause precipitation when mixed with an aqueous solution of the cobalt precursor is preferable.

By the addition of base, the pH of the aqueous cobalt precursor solution may be adjusted to a range of, for example, at least about 10, specifically at least about 11, more specifically about 10.5 to 11.5.

In this manner, when a pH-adjusted aqueous solution of a Co(III) precursor is prepared, this aqueous solution is combined with the pH-adjusted aqueous dispersion of alkali metal-treated silica (step e).

The mixing ratio of the pH-adjusted aqueous solution of cobalt precursor and the pH-adjusted aqueous dispersion of alkali metal-treated silica may be determined in consideration of the amount in which the cobalt ions in the aqueous solution of cobalt precursor can be fixed in a form of single atom (particularly single-atom of a single layer) on the surface of the alkali metal-treated support. In this regard, cobalt ions may be loaded in the form of single atom by at most about 2% to 3% by weight on the silica surface. However, all of the cobalt precursor used cannot be fixed onto the surface of the silica-based support in practice. Thus, an excess of a cobalt (Co(III)) precursor larger than the theoretical amount may be dissolved.

In an exemplary embodiment, the mixing ratio of the aqueous solution of cobalt precursor and the aqueous dispersion of alkali metal-treated silica may be adjusted so that the amount of the cobalt precursor is in a range of about 1% to 20% by weight, specifically about 2% to 10% by weight, more specifically about 3% to 8% by weight based on the weight of silica. The weight ratio of cobalt:alkali metal in the mixing process may be adjusted in a range of, for example, about 2000:1 to 1:1, specifically about 1000:1 to 10:1, more specifically about 500:1 to 100:1.

As a result, at least a part of the cobalt ions can be electrostatistically adsorbed onto the surface of the silica on which alkali metal ions have been adsorbed. Moreover, it is possible to obtain an aqueous dispersion of silica on which the alkali metal ions (e.g., $K^+$ ions) and the cobalt ions ($Co^{3+}$ ions) can be each fixed or immobilized in the single-atom form. In particular, the cobalt having an oxidation number of 3+ (or $Co^{3+}$) as a precursor can strongly bind only to the sites of silica surface at which 3-membered siloxane rings exist, due to the alkali metal ions already introduced to the silica support by the alkali treatment while the deposition of cobalt is prevented at the other sites. In other words, the pre-treatment of the silica-based support with the alkali metal restrains the sites available for cobalt deposition.

On the other hand, when cobalt is supported without treatment with an alkali metal, cobalt ions are weakly attached to an undesired surface site of the silica support, for example, a site at which isolated silanol groups exist. The cobalt thus unstably supported undergoes polygomerization (dimerization) with other cobalt during subsequent dehydrogenation reactions and aggregates, inducing a phenomenon of particle formation and acting to lower the catalytic activity.

According to an exemplary embodiment, the combination of two aqueous fluids (i.e., the aqueous silica dispersion and the aqueous cobalt precursor solution) may be performed under stirring, the stirring speed may be in a range of, for example, about 200 to 500 rpm, specifically about 250 to 400 rpm, and the stirring time may be in a range of, for example, at least about 3 minutes, specifically at least about 5 minutes, more specifically about 5 to 10 minutes, but the stirring conditions are not necessarily limited to the above conditions. A temperature for the mixing may be set to be, for example, about 10 to 40° C., particularly about 20 to 30° C., and more particularly room temperature, without limitations thereto.

Then, a step of removing as much alkali metal and cobalt remaining unfixed in a single-atom form onto the surface of the cobalt- and alkali metal-containing silica from the mixed aqueous medium as possible may be conducted (step f). This process, which makes the method of the present disclosure different from the conventional impregnation method, is to leave only the alkali metal (or alkaline ions) and cobalt (or $Co^{3+}$) that are fixed in single-atom forms onto the silica surface by electrical interaction while eliminating the others. As in the conventional impregnation method, for example, a cobalt precursor attached in a bulk state on a silica surface induces reduction, aggregation, etc., that lower catalytic activity, during the dehydrogenation.

In full consideration of the foregoing, the solid (the silica on which the cobalt precursor and alkali metal are adsorbed (immobilized)) in the combined dispersion can be separated from the liquid through any conventional solid-liquid separation technique such as settling, filtration, etc., and as necessary, the separated solid may be subjected to repeated cycles of adding water, particularly distilled water, stirring, and separating according to an exemplary embodiment. By way of example, the separated solid may be washed with water, particularly distilled water at least once, particularly two or more times to remove as much the alkali metal and cobalt precursor remain unattached as possible. Thereafter, the obtained solid may be dried, at a temperature of, for example, about 10° C. to 40° C., specifically about 20° C. to 30° C., more specifically, room temperature without limitations thereto. At this time, the cobalt ions still retain an oxidation number of +3.

As a subsequent step, the cobalt- and alkali metal-adsorbed (immobilized) silica can be converted into a dehydrogenation catalyst through a heat (or thermal) treatment (step f). At this time, the heat treatment may be performed in an oxygen-containing atmosphere, at, for example, about 250° C. to 1000° C., specifically about 275° C. to 800° C., more specifically about 300° C. to 600° C. In the present embodiment, the cobalt having an oxidation number of 3+ that has been adsorbed on silica is converted into cobalt having an oxidation number of 2+ as the heat treatment of the cobalt- and alkali metal-adsorbed (immobilized) silica is performed.

However, an additional drying step may be optionally performed prior to the heat treatment step under an oxygen-containing atmosphere, and the additional drying temperature at this time may be in a range of, for example, about 50° C. to 150° C., specifically about 120° C. to 150° C. In the course of such a relatively high-temperature drying, at least a part of the cobalt atoms having an oxidation number of 3+ may be partially reduced to cobalt atoms having an oxidation number of 2+ in advance.

In this regard, without being bound by a particular theory, the reason why the cobalt retains an oxidation number of 2+ after heat treatment may be explained as follows.

For cobalt with an oxidation number of 3+, only the octahedral structure is possible because six electrons occupy the outmost orbital to enable the formation of six bonds. When the cobalt is reduced to 2+, seven electrons exist in the outmost orbital, thus mainly forming a tetrahedral structure, while an octahedral structure is also possible as in CoO. According to the present embodiment, it is supposed that the cobalt is reduced to 2+ to form a tetrahedral structure because it should structurally bind to the 3-membered siloxane group. On the other hand, in order to return back to 3+, the cobalt should form an octahedron in cooperation with its surroundings. At this time, silicon (Si) does not have any structure other than a tetrahedron in nature, which is in discord with the octahedral structure of cobalt, and thus making it difficult to convert the reduced cobalt to the oxidized state 3+. In contrast, the deactivation arises when the linkage (communication) to Si is cleaved to cause Co metal to aggregate or agglomerate alone. Accordingly, it is considered that the formation of an oxide by contact with oxygen could result in $Co_3O_4$ containing cobalt of the oxidation state 3+.

The heat treatment time is not particularly limited as long as it is a sufficient time for converting 3+ cobalt into 2+ cobalt but may be in a range of, for example, about 2 to 12 hours, specifically about 2.5 to 8 hours, more specifically about 3 to 4 hours. The cobalt with the oxidation number 2+, converted by heating at a predetermined temperature or higher during the heat treatment step, is not returned back to the oxidation number 3+ even though the heat treatment is continued in an oxygen-containing (or oxidation) atmosphere (or calcining atmosphere). The reason is because the single-atom cobalt needs to retain a tetrahedral structure. Furthermore, even when the catalyst is applied to the dehydrogenation conducted at a predetermined temperature or higher, the oxidation state remains unchanged, implying that the catalyst according to the present embodiment is resistant to reduction.

Dehydrogenation

According to another embodiment of the present disclosure, there is provided a process of converting a paraffin, particularly light paraffin (more particularly light paraffin of 2 to 5 carbon atoms) to the corresponding olefin by using the aforementioned cobalt-based single-atom catalyst. Particularly, the light paraffin may contain propane. In this regard, a feedstock may be provided as a gas phase.

At this time, it should be noted that when applied even to a feedstock containing a high content of paraffin, the catalyst can achieve better conversion and selectivity. By way of example, the content of paraffin in a feedstock may be, for example, at least about 50% by volume, particularly at least about 70% by volume, more particularly at least about 80% by volume, and higher than about 99% by volume. This makes a difference from the experimental results in which a feedstock containing at most about 20% by volume is subjected to dehydrogenation in the presence of the conventional single-atom catalyst (e.g., Zn catalyst).

In the dehydrogenation according to an exemplary embodiment, the reaction temperature may range, for example, from about 500 to 700° C., particularly from about 550 to 650° C., and more particularly from about 570 to 620° C. In addition, a pressure of, for example, about 0.3 to 2 bar, particularly about 0.4 to 1.5 bar, and more particularly about 0.5 to 1 bar may be set for the dehydrogenation. As for the gas hourly space velocity (GHSV) in the standard state, its range may be chosen to be, for example, about 100 to 2000 $hr^{-1}$, particularly about 200 to 1500 $hr^{-1}$, and more particularly about 300 to 1000 $hr^{-1}$ in a standard condition. The dehydrogenation conditions may vary depending on kinds of paraffins in the feedstock, the loading amounts of active metals and alkali metals, respectively, and the ratio therebetween in the catalyst, etc.

According to an exemplary embodiment, the conversion and selectivity in the dehydrogenation may be, for example, at least about 30% (particularly at least about 40%), and at least about 70% (particularly at least about 80%), respectively.

A better understanding of the present disclosure may be obtained through the following examples which are set forth to illustrate, but are not to be construed as limiting the present disclosure.

Examples

The analysis instruments and analysis methods used in the present Examples are as follows.

EXAFS

In order to investigate the single-atom cobalt in the cobalt single-atom catalyst and to analyze surroundings around the single-atom cobalt, Co K-edge (7.709 keV) X-ray absorption spectroscopy (XAFS) was measured and recorded at the 8 C beamline (nano-XAFS (X-ray absorption spectroscopy), 4-20 keV, 1012 photons/sec) of the Pohang Light Source (PAL PLS-II). The gas was controlled to set the absorption rates of $I_0$ and $I_t+I_r$ at 15% and 85%, respectively. The monochromator was detuned to 70%. All the specimens except for a reference (0.1 mm) were each powdered, loaded to a 2 mm slit, and made flattened before measurement in a transmission mode.

Calculation of Conversion and Selectivity

Conversion of propane and selectivity according to Equations 1 and 2, below.

$$\text{Conversion Rate of Propane} = \frac{\text{Weight of propane in reactant} - \text{Weight of unconverted propane in product}}{\text{Weight of propane in reactant}} \times 100 \quad \text{[Equation 1]}$$

$$\text{Selectivity for propylene (\%)} = \frac{\text{Weight of propylene in product}}{\text{Weight of propane in reactant} - \text{Weight of unconverted propane in product}} \times 100 \quad \text{[Equation 2]}$$

Preparation Example 1

First, 20 g of commercially available silica was dispersed in 200 ml of distilled water, 0.144 g of KOH was dissolved in the dispersion, and the resultant dispersion was stirred for 30 minutes to prepare an aqueous silica dispersion. Thereafter, the pH of the dispersion was adjusted to 11 by adding concentrated ammonia water at 28% by weight (Samchun Chemical Co., Ltd.) to the aqueous silica dispersion, thereby producing a pH-adjusted aqueous dispersion of potassium-treated silica.

Separately, 5 g of cobalt precursor ($Co(NH_3)_6Cl_3$) was dissolved in 50 ml of distilled water in a beaker, the pH of the solution was adjusted to 11 by adding concentrated ammonia water at 28% by weight (Samchun Chemical Co., Ltd.) to the solution, thereby producing a pH-adjusted aqueous solution of cobalt precursor.

Next, the pH-adjusted aqueous solution of cobalt precursor was quickly added to the pH-adjusted aqueous dispersion of potassium-treated silica and the mixture was stirred at room temperature for 10 minutes. After the stirred sample was left to stand for 5 minutes, the liquid phase was discarded, then 200 ml of distilled water was poured remaining sample again, and the mixture was stirred again for 10 minutes. After the stirred sample was left to stand again and the liquid phase was discarded, the remaining sample was filtered under reduced pressure and washed with distilled water several times.

The filtered sample was dried at room temperature and then further dried at 125° C. The dried sample was heated to 300° C. at a heating rate of 5° C. per minute and then subjected to a heat treatment in the air for 3 hours, thereby producing a dehydrogenation catalyst (Co, K@$SiO_2$ catalyst).

Comparative Preparation Example 1

In 200 ml of distilled water, 20 g of silica used in Preparation Example 1 was dispersed, and the pH of the dispersion was adjusted to 11 by adding concentrated ammonia water at 28% by weight (Samchun Chemical Co., Ltd.) to the dispersion, thereby producing a pH-adjusted aqueous silica dispersion.

Separately, 5 g of cobalt precursor ($Co(NH_3)_6Cl_3$) was dissolved in 50 ml of distilled water in a beaker, the pH of the solution was adjusted to 11 by adding concentrated ammonia water at 28% by weight (Samchun Chemical Co., Ltd.) to the solution, thereby producing a pH-adjusted aqueous solution of cobalt precursor.

Next, the pH-adjusted aqueous solution of cobalt precursor was quickly added to the pH-adjusted aqueous dispersion of silica and the mixture was stirred at room temperature for 10 minutes. After the stirred sample was left to stand for 5 minutes, the liquid phase was discarded, then 200 ml of distilled water was poured to the remaining sample again, and the mixture was stirred again for 10 minutes. After the stirred sample was left to stand again and the liquid phase was discarded, the remaining sample was filtered under reduced pressure and washed with distilled water several times.

The filtered sample was dried at room temperature and then further dried at 125° C. The dried sample was heated to 300° C. at a heating rate of 5° C. per minute and then subjected to a heat treatment in the air for 3 hours, thereby producing a dehydrogenation catalyst (Co@$SiO_2$ catalyst).

The contents of cobalt and potassium in the catalysts produced according to Preparation Example 1 and Comparative Preparation Example 1, respectively, are presented in Table 2 below.

TABLE 2

|  | Co content (wt %) | K content (ppm) |
| --- | --- | --- |
| Comparative Preparation Example 1 | 3.36 | n/d |
| Preparation Example 1 | 2.86 | 60.1 |

Figure 1:
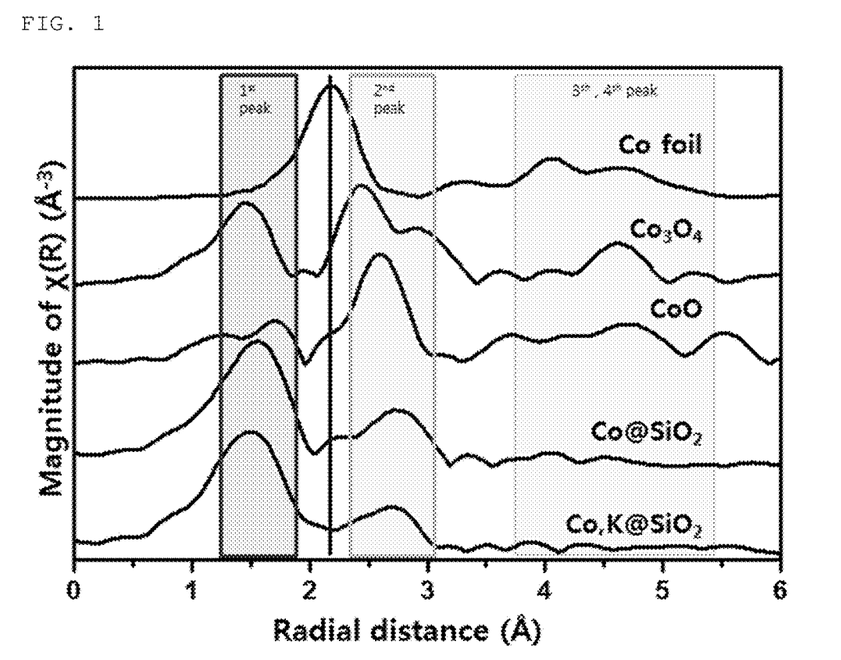
FIG. 1 is a graph showing the results of EXAFS analysis for cobalt-based catalysts prepared according to Preparation Example 1 and Comparative Preparation Example 1, respectively.

The EXAFS analysis results for the cobalt-based catalysts produced according to Preparation Example 1 and Comparative Preparation Example 1, respectively, are illustrated in FIG. 1.

Referring to FIG. 1, in the case of Co metal (Co foil), a peak denoted by a blue line is strongly expressed, and this is a characteristic that appears when Co metal exists as Co—Co bond.

Further, as the peaks of $Co_3O_4$ and CoO that correspond to ordinary Co oxides, the first peak for Co—O and the second peak for Co—Co were observed. In the case of an oxide, the second peak is well developed since the oxide exists as a crystalline entity in the particle and the structure of the unit cell is repeated.

On the other hand, in both the Co@$SiO_2$ catalyst and Co, K@$SiO_2$ catalyst produced according to Comparative Preparation Example 1 and Preparation Example 1, respectively, the first peak is well developed but the second peak is significantly attenuated, which indicates that Co atoms are away from each other, with no bonds formed therebetween. In view of the Si—O bond which supports Co, the weak peaks are considered to come from the Co—Si bond. Consequently, it is suggested that Co exists in the form of single atom in both the Co@$SiO_2$ catalyst (Comparative Preparation Example 1) and the Co, K@$SiO_2$ catalyst (Preparation Example 1).

Experimental Example 1

In the present Experimental Example, a dehydrogenation for synthesizing olefins from a reactant gas containing paraffins at a high content was conducted in the presence of cobalt-based catalysts produced according to Comparative Preparation Example 1 and Preparation Example 1, respectively.

The dehydrogenation for catalyst evaluation was carried out using a ¾-inch quartz tube reactor (¾ inches for diameter in the catalyst loading region and ¼ inch for diameter for the other tube region). The flow rate of each gas was adjusted using a mass flow controller, and the product gas from the reactor was analyzed using an online gas chromatography apparatus (50 m HP-PLOT column).

After 5 cc (about 3.3 g) of catalyst was weighed and loaded in the reaction tube with quartz wool, and the temperature was raised from room temperature to 590° C. at a rate of 5° C./min while allowing $N_2$ (99.999%, DAESUNG INDUSTRIAL GASES CO., LTD.) to flow at a flow rate of 100 cc/min. Thereafter, the condition was maintained for 1 hour for stabilization during which a micro-air pump installed at the rear of the reactor was used to reduce the pressure in the reaction tube to about 0.5 bar.

For dehydrogenating paraffin, the reactant gas containing 99.5% propane (regas) was introduced at a flow rate of 20 cc/min into the reactor. The composition of the gas from the reactor was analyzed using FID (flame ionization detector). The results are illustrated in FIG. 2.

Figure 2A:
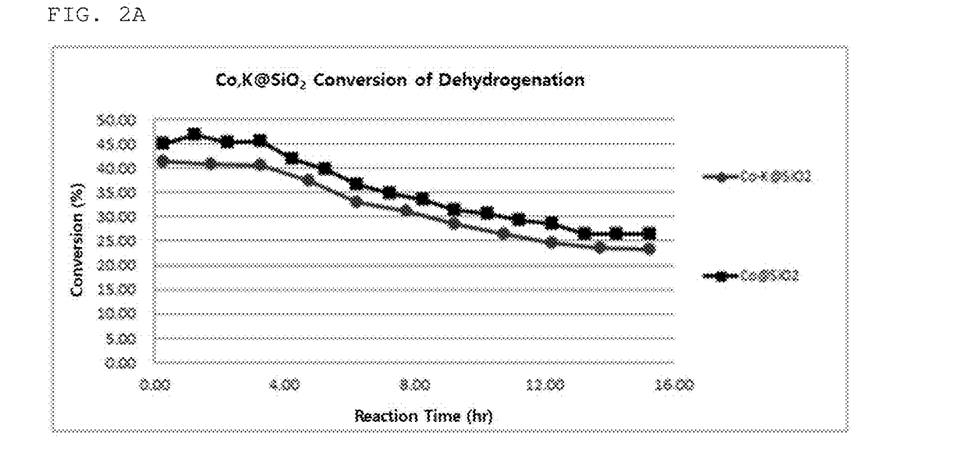
FIGS. 2A and 2B, respectively, are a graph showing the conversion and selectivity measured for the propane dehydrogenation according to Experimental Example 1 in the presence of cobalt-based single-atom catalysts prepared by Preparation Example 1 and Comparative Preparation Example 1, respectively.
Figure 2B:
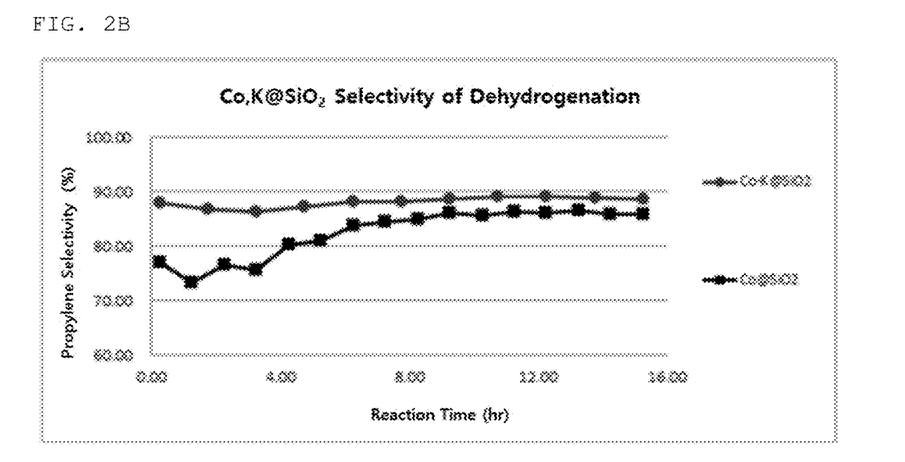

According to FIG. 2, as a result of the dehydrogenation, in the case of the catalyst according to Preparation Example 1, the conversion by the catalyst was slightly lower than that by the catalyst according to Comparative Preparation Example 1, but the initial selectivity was remarkably higher. This means that the yield of olefins is equal or higher.

Figure 3:
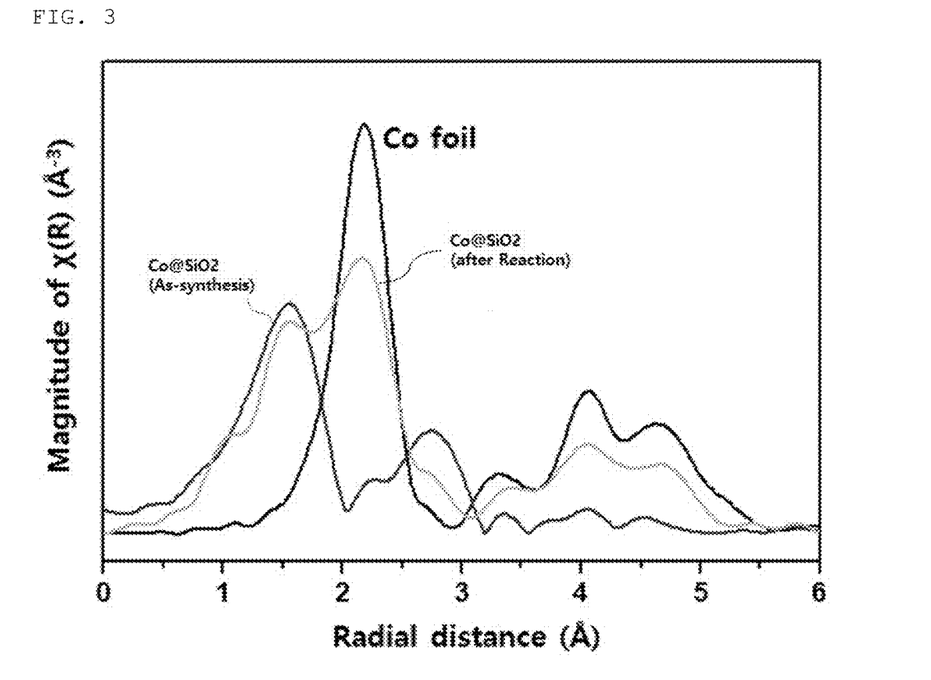
FIG. 3 is a graph showing the results of EXAFS analysis for the catalyst before and after the propane dehydrogenation according to Experimental Example 1 in the presence of the cobalt-based single-atom catalyst prepared by Comparative Preparation Example 1.

Furthermore, when the propane dehydrogenation is conducted in Experimental Example 1 in the presence of the cobalt-based Preparation Example 1, the results attained by observing the changes before and after the reaction by EXAFS are illustrated in FIG. 3.

Referring to FIG. 3, as a result of the dehydrogenation, in the case of the catalyst according to Comparative Preparation Example 1, Co did not exist in the form of single atom and was reduced to partially form Co metal after the dehydrogenation.

Experimental Example 2

In the present Experimental Example, in order to evaluate the thermal stability of the cobalt-based catalysts produced according to Preparation Example 1 and Comparative Preparation Example 1, respectively, a heat treatment was performed at a high temperature. Specifically, the heat treatment was performed at 800° C. for 3 hours in an air atmosphere. The results attained by observing the changes of the catalysts after the heat treatment together with the changes of the catalysts after the propane dehydrogenation conducted in Experimental Example 1 by EXAFS are illustrated in FIG. 4.

Figure 4:
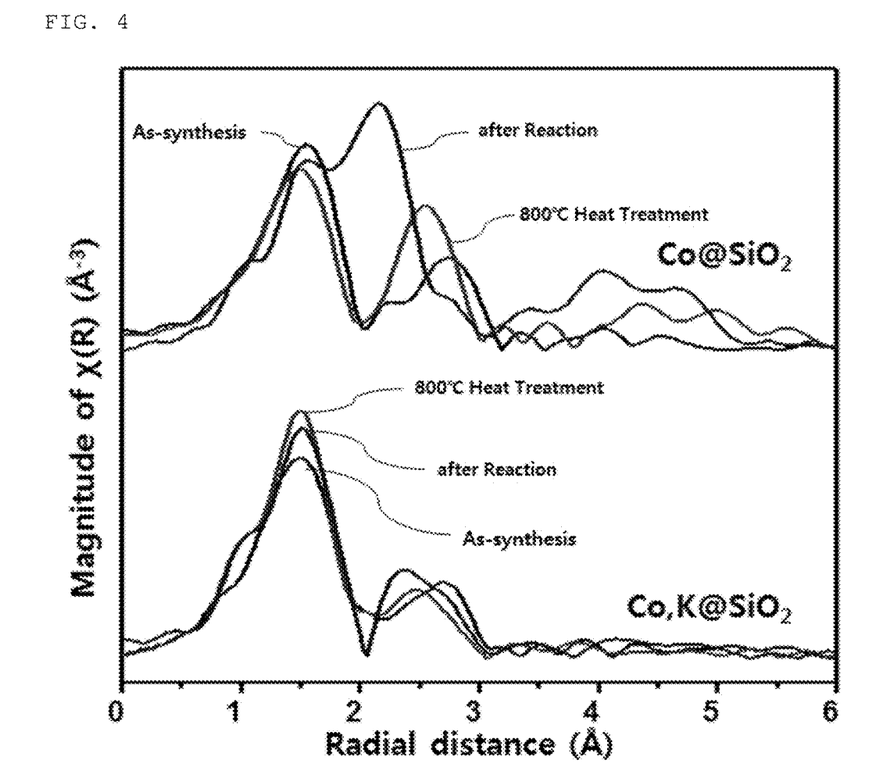
FIG. 4 is a graph showing the results of EXAFS analysis for the catalyst after the propane dehydrogenation according to Experimental Example 1 in the presence of cobalt-based single-atom catalysts by Preparation Example 1 and Comparative Preparation Example 1, respectively, and the heat treatment at a high temperature according to Experimental Example 2.

Referring to FIG. 4, it can be seen that Co exists in the form of single atom even after the dehydrogenation or a high-temperature heat treatment when silica is treated with K before Co in the form of single atom is loaded onto silica as in Preparation Example 1, but the Co state changes after the dehydrogenation or the heat treatment when using the catalyst according to Comparative Preparation Example 1.

Comparative Preparation Example 2

In the present Preparation Example, a cobalt-based single-atom catalyst was treated with an alkali metal by an impregnation method. Specifically, 5 g of the cobalt-based Preparation Example 1 and 0.065 g of $K(NO_3)$ as a potassium precursor were weighed and mixed together for 1 hour using a roll mixer, 5 ml of distilled water was added thereto, and the mixture was stirred for 30 minutes. The resulting dispersion was heated to 70° C. while performing stirring to remove moisture, and then sufficiently dried in an oven maintained at 90° C. The dried sample was subjected to a heat treatment at 300° C. for 3 hours, thereby producing a $K/Co@SiO_2$ catalyst.

Comparative Preparation Example 3

In the present Preparation Example, a cobalt-based single-atom catalyst to which an alkali metal was added was produced by a method in which an alkali metal was added to a silica support by a conventional impregnation method and then cobalt was loaded on the silica support.

First, 5 g of silica and 0.065 g of $K(NO_3)$ as a potassium precursor were weighed and mixed together for 1 hour using a roll mixer, 5 ml of distilled water was added thereto, and the mixture was stirred for 30 minutes. The resulting dispersion was heated to 70° C. while performing stirring to remove moisture, and then sufficiently dried in an oven maintained at 90° C. The dried sample was subjected to a heat treatment at 300° C. for 3 hours, thereby producing a silica support to which an alkali metal was added. The support thus produced was dispersed in 50 ml of distilled water, and the pH of the dispersion was adjusted to 11 by adding concentrated ammonia water at 28% by weight (Samchun Chemical Co., Ltd.) to this.

Separately, 5 g of cobalt precursor $(Co(NH_3)_6Cl_3)$ was dissolved in 50 ml of distilled water in a beaker, the pH of the solution was adjusted to 11 by adding concentrated s ammonia water at 28% by weight (Samchun Chemical Co., Ltd.) to the solution, thereby producing a pH-adjusted aqueous solution of cobalt precursor.

Next, the pH-adjusted aqueous solution of cobalt precursor was quickly added to the pH-adjusted aqueous silica dispersion and the mixture was stirred at room temperature for 10 minutes. After the stirred sample was left to stand for 5 minutes, the liquid phase was discarded, then 100 ml of distilled water was poured to the remaining sample again, and the mixture was stirred again for 10 minutes. After the stirred sample was left to stand again and the liquid phase was discarded, the remaining sample was filtered under reduced pressure and washed with distilled water several times.

The filtered sample was dried at room temperature and then further dried at 125° C. The dried sample was heated to 300° C. at a heat rate of 5° C. per minute and then subjected to a heat treatment in the air for 3 hours, thereby producing a dehydrogenation catalyst ($Co@K/SiO_2$ catalyst).

Experimental Example 3

In the present Experimental Example, the dehydrogenation for producing olefins from a reactant gas containing paraffins at a high content was conducted using three kinds of cobalt-based single-atom catalysts, to which an alkali metal was added, produced according to Preparation Example 1 and Comparative Preparation Examples 2 and 3, respectively.

In order to quickly confirm the conversion, selectivity, and deactivation rate by subjecting the three kinds of catalysts to the reaction under more severe conditions, 0.8 cc (about 0.5 g) of the catalyst was loaded a ¾-inch quartz tube reactor (¾ inches for diameter in the catalyst loading region and ¼ inch for diameter for the other tube region) using quartz wool, and the temperature was raised from room temperature to 575° C. at a rate of 5° C./min while allowing $N_2$ (99.999%, DAESUNG INDUSTRIAL GASES CO., LTD.) to flow at a flow rate of 100 cc/min. Thereafter, the condition was maintained for 1 hour for stabilization, and the pressure was not reduced in order to conduct the reaction under severe conditions.

After the temperature of the reactor was stabilized, 99.5% propane as the reactant gas was injected into the reactor at a flow rate of 3 cc/min for the dehydrogenation of paraffin. The flow rate of each gas was adjusted using a mass flow controller, and the product gas from the reactor was analyzed using an online gas chromatography apparatus (50 m HP-PLOT column). The composition of the product gas from the reactor was analyzed using a flame ionization detector (FID). The results are illustrated in FIG. 5.

Figure 5A:
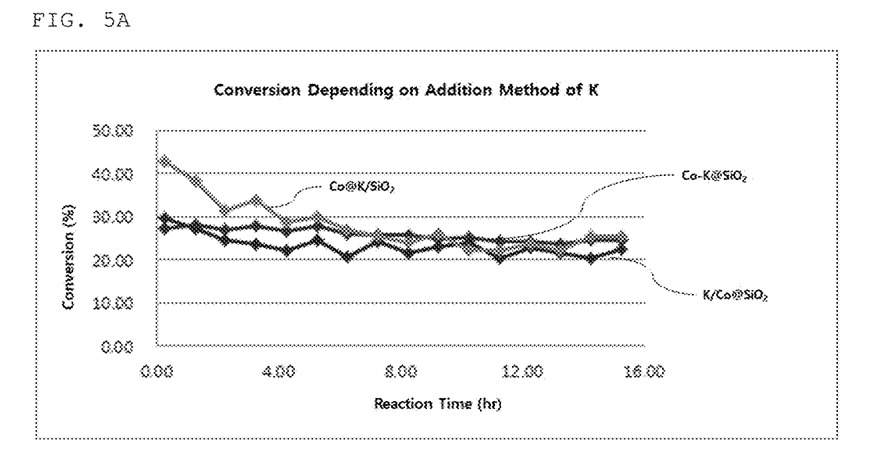
FIGS. 5A and 5B, respectively, are a graph showing the conversion and selectivity measured for the propane dehydrogenation according to Experimental Example 3 using the three cobalt-based single-atom catalysts, to which alkali metals are attached, prepared by Preparation Example 1 and Comparative Preparation Examples 2 and 3.
Figure 5B:
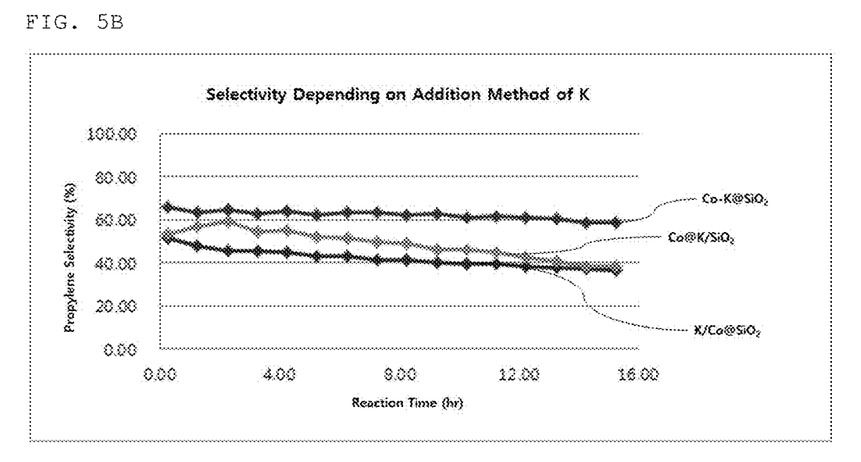

From the results of FIG. 5, it has been confirmed that the activity of the catalyst is deteriorated during the dehydrogenation or the effect of stabilizing cobalt is not observed when potassium (K) is post-treated after cobalt in the form of single atom is supported (Comparative Preparation Example 2) and when cobalt in the form of single atom is supported after silica is pretreated with potassium (K) by the conventional impregnation method (Comparative Preparation Example 3).

Experimental Example 4

In the present Experimental Example, a dehydrogenation for producing olefins from a reactant gas containing paraffins at a high content was conducted plural times using the cobalt-based catalyst produced according to Preparation Example 1.

The dehydrogenation for catalyst evaluation was conducted using a ¾-inch quartz tube reactor (¾ inches for diameter in the catalyst loading region and ¼ inch for diameter for the other tube region). The flow rate of each gas was adjusted using a mass flow controller, and the product gas from the reactor was analyzed using an online gas chromatography apparatus (50 m HP-PLOT column).

After 5 cc (about 3.3 g) of catalyst was weighed and loaded in the reaction tube with quartz wool, and the temperature was raised from room temperature to 590° C. at a rate of 5° C./min while allowing $N_2$ (99.999%, DAESUNG INDUSTRIAL GASES CO., LTD.) to flow at a flow rate of 100 cc/min. Thereafter, the condition was maintained for 1 hour for stabilization during which a micro-air pump installed at the rear of the reactor was used to reduce the pressure in the reaction tube to about 0.5 bar.

For the initial dehydrogenation, the reactant gas containing 99.5% propane (regas) was injected into the reactor at a flow rate of 20 cc/min, and this state was maintained for 100 minutes. After the dehydrogenation was conducted for 100 minutes, the inside of the reaction tube was purged in an atmosphere of $N_2$ at 100 cc/min for 30 minutes.

In the next catalyst regeneration step, air (99.999%) was allowed to flow at a flow rate of 100 cc/min to remove coke generated in the reaction step, and then the inside of the reaction tube was purged by allowing $N_2$ gas to flow at a flow rate of 100 cc/min for another 30 minutes. The results attained by observing the changes of catalyst by EXAFS when the four steps of reaction-purge-regeneration-purge are repeated 15 times are illustrated in FIG. 6.

Figure 6:
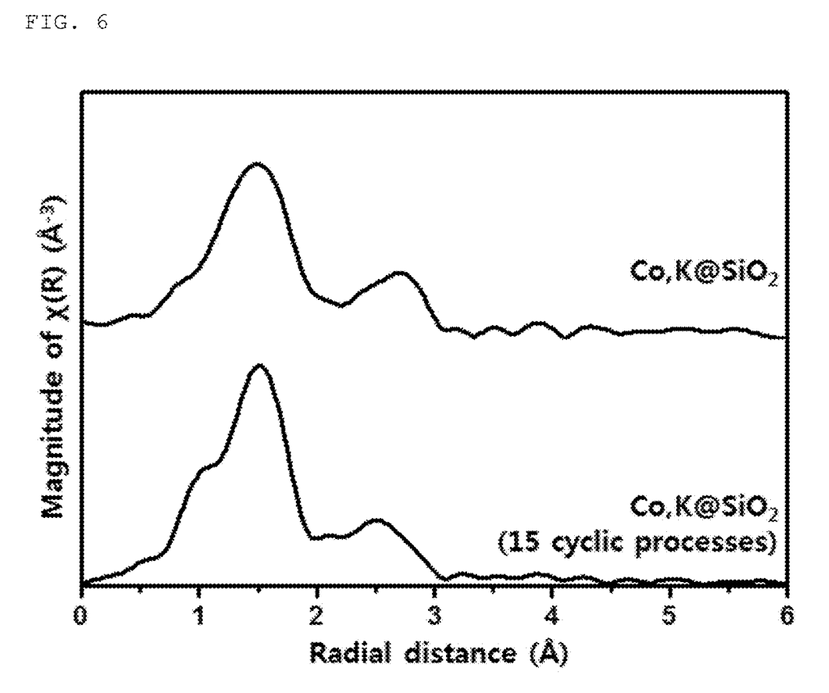
FIG. 6 is a graph showing the results of EXAFS analysis for the catalyst after the propane dehydrogenation-regeneration process is repeated 15 times according to Experimental Example 4 using a cobalt-based single-atom catalyst prepared by Preparation Example 1.

Referring to FIG. 6, it can be seen that the cobalt (Co) in the catalyst is stably maintained in the form of single atom even when the reaction-regeneration is repeated 15 times at a high temperature of about 600° C. in the case of the catalyst according to Preparation Example 1.

Simple modifications or changes of the present invention can be easily utilized by those skilled in the art, and all such modifications or changes can be considered to be included in the scope of the present invention.

The invention claimed is:

1. A method for preparing a cobalt single-atom catalyst, the method comprising:
   a) preparing a silica-containing aqueous dispersion;
   b) dissolving a salt of an alkali metal in the silica-containing aqueous dispersion to give an aqueous dispersion of alkali metal-treated silica;
   c) adjusting a pH of the aqueous dispersion of alkali metal-treated silica to at least 10 by adding an ammonium-containing base to the aqueous dispersion to give a pH-adjusted aqueous dispersion of alkali metal-treated silica, wherein at least a part of alkali metal ions are electrostatically adsorbed on the surface of the silica;
   d) separately preparing an aqueous solution of a cobalt precursor having an oxidation number of 3+ and adjusting a pH of the aqueous solution of a cobalt precursor to at least 10 by adding a base to the aqueous solution to give a pH-adjusted aqueous cobalt precursor solution;
   e) combining the pH-adjusted aqueous dispersion of alkali metal-treated silica with the pH-adjusted aqueous cobalt precursor solution to give an aqueous dispersion in which at least a part of cobalt ions having an oxidation number of 3+ are electrostatically adsorbed on the surface of the alkali metal ion-adsorbed silica;
   f) removing an alkali metal and cobalt that are not adsorbed on the surface of the silica from the aqueous dispersion of the cobalt ion, alkali metal ion-adsorbed silica; and
   g) heat treating the cobalt ion, alkali metal ion-adsorbed silica resulting from the step f),
   wherein the cobalt having an oxidation number of 2+ and the alkali metal having an oxidation number of 1+, respectively, exist in an isolated form of single atom on the silica while the cobalt having an oxidation number of 2+ forms a tetrahedrally coordinated at the three-membered siloxane ring present on the surface of silica,
   wherein a content of an alkali metal in the catalyst is in a range of 0.004% to 1% by weight, and
   wherein a weight ratio of cobalt (Co)/alkali metal in the catalyst is in a range of 1 to 2000, and wherein the silica is amorphous silica.

2. The method according to claim 1, wherein a content of silica in the silica-containing aqueous dispersion prepared in the step a) is in a range of 1% to 30% by weight.

3. The method according to claim 1, wherein the alkali metal is at least one selected from the group consisting of sodium (Na), potassium (K), and cesium (Cs), and
   the salt of an alkali metal is at least one selected from the group consisting of a hydroxide, a nitrate, a chloride, a carbonate, and a sulfate of an alkali metal.

4. The method according to claim 1, wherein a content of the salt of an alkali metal in the step b) is in a range of 0.001% to 3% by weight based on a weight of silica in the aqueous dispersion.

5. The method according to claim 1, wherein the cobalt precursor in the step d) is a precursor containing a cobalt (Co(III)) complex ion having an oxidation number of 3+, and
   a concentration of the cobalt precursor in the aqueous solution of cobalt precursor is in a range of 0.1% to 20% by weight.

6. The method according to claim 5, wherein $Co(NH_3)_6Cl_3$ is directly used or a precursor containing a cobalt complex ion, which is obtained by treating at least one cobalt compound selected from the group consisting of $Co(NO_3)_2$, $CoCl_2$, and $Co(acac)_3$ with ammonia water and performing filtering as the cobalt precursor.

7. The method according to claim 1, wherein a mixing ratio of the pH-adjusted aqueous solution of cobalt precursor and the pH-adjusted aqueous dispersion of alkali metal-treated silica in the step e) is adjusted so that a content of the cobalt precursor is 1% to 20% by weight based on a weight of silica.

8. The method according to claim 1, wherein the heat treatment is performed in an oxygen-containing atmosphere under a temperature condition of 250° C. to 1000° C.

9. The method according to claim 1, further comprising drying the cobalt ion, alkali metal ion-adsorbed silica at 50° C. to 150° C. prior to the step g),
   wherein an oxidation number of cobalt ions after drying is partially reduced to 2+.

10. The method according to claim 1, wherein a content of cobalt in the catalyst is in a range of 0.1% to 10% by weight.

11. The method according to claim 1, wherein the step e) is performed at a temperature in a range of 10° C. to 40° C.

\* \* \* \* \*

UNITED STATES PATENT AND TRADEMARK OFFICE
CERTIFICATE OF CORRECTION

PATENT NO. : 12,161,999 B2
APPLICATION NO. : 17/289271
DATED : December 10, 2024
INVENTOR(S) : Ho Won Lee et al.

It is certified that error appears in the above-identified patent and that said Letters Patent is hereby corrected as shown below:

In the Claims

Column 18, Line 52, Claim 3, before "the salt" insert -- wherein --

Column 18, Line 62, Claim 5, before "a" insert -- wherein --

Signed and Sealed this
Twenty-second Day of July, 2025

Coke Morgan Stewart
*Acting Director of the United States Patent and Trademark Office*